United States Patent [19]

Giurtino

[11] 4,207,923
[45] Jun. 17, 1980

[54] FLUID VALVE

[75] Inventor: Joel F. Giurtino, Littleton, Colo.

[73] Assignee: Cobe Laboratories, Inc., Lakewood, Colo.

[21] Appl. No.: 937,851

[22] Filed: Aug. 29, 1978

[51] Int. Cl.² .......................................... F16K 11/085
[52] U.S. Cl. ................................ 137/625.47; 251/181; 251/309
[58] Field of Search ............................. 251/181, 309; 137/625.47, 625.41

[56] References Cited

U.S. PATENT DOCUMENTS

| 3,185,179 | 5/1965 | Harautuneian | 137/625.47 |
| 3,269,696 | 8/1966 | Horton | 251/181 |
| 3,481,367 | 12/1969 | Deuschle | 137/625.47 |
| 3,750,704 | 8/1973 | Burke et al. | 137/625.47 |
| 3,774,604 | 11/1973 | Danielsson | 137/625.47 X |
| 3,788,599 | 1/1974 | Cloyd | 251/181 |

FOREIGN PATENT DOCUMENTS 23883 of 1903 United Kingdom .................... 251/181

Primary Examiner—Arnold Rosenthal

[57] ABSTRACT

A fluid valve with a valve body and core, the core being retained in the valve body by resilient fingers which extend from the body and snap past a lip on the valve core on insertion of the core into the body.

8 Claims, 3 Drawing Figures

FLUID VALVE

FIELD OF THE INVENTION

This invention relates to fluid valves, particularly to stopcock valves wherein fluid flow is shut off by a 90 degree turn of a valve handle.

BACKGROUND OF THE INVENTION

Stopcocks have long been used to meter fluids. A core with an internal passage is received in the bore of a valve body, and rotation of the core by means of an attached handle brings the internal passage into or out of communication with fluid passages in the valve body. It is necessary in any such stopcock to provide means to longitudinally retain and align the core in the valve body. Conventionally, a separate locking member, installed after inserting the core into the valve body, has provided the desired retention.

A stopcock manufactured by Pharmaseal, Inc., Glendale, Calif. comprises a molded tubular valve body and a core held together by a friction cap pressed onto one end of the core after its installation through the valve body. Integral fittings are secured to the exterior of the tubular body, and the core and tubular interior of the valve body are both slightly tapered to allow the slightly larger core to achieve an interference fit when the two pieces are axially forced together.

SUMMARY OF THE INVENTION

I have discovered that core retention can be had in a stopcock without the added manufacturing cost of a separate locking member. Instead, the core is retained in the valve body by means of one or more resilient fingers which extend from the valve body and cooperate with a lip portion on the core, the fingers snapping outwardly away from the lip portion during installation of the core and acting against a surface of the lip portion during operation to retain the core and align it with the valve body.

In a preferred embodiment, a seat on the valve body cooperates with a bearing surface on the core to prevent movement of the core in the longitudinal direction opposite to that of the movement prevented by the resilient fingers, thereby locking the core against movement in either longitudinal direction; four fingers extend from the valve body and are peripherally spaced around the bore in which the core is received, each finger being angled radially inward sufficiently to engage an annular lip on the longitudinal end of the core; ridges radially extending from the core cooperate with the grooves formed by spaces between the fingers to provide tactile feedback to the user of the angular position of the core; and the core and bore are cylindrical.

The invention simplifies and reduces manufacturing costs by reducing the number of essential component parts required to two (a valve body with integral fingers and a valve core with an integral lip portion) and by allowing assembly to be accomplished with one simple longitudinal insertion of the valve core. In addition core retention reliability is improved over that of friction-based retention means. And in the preferred embodiment the cylindrical shape of the core prevents fluid pressure from forcing the core out of the body, which can occur with a frustoconical core.

PREFERRED EMBODIMENT

I turn now to description of the structure and operation of a preferred embodiment of the invention, after first briefly describing the drawings.

DRAWINGS

DESCRIPTION

Figure 1:
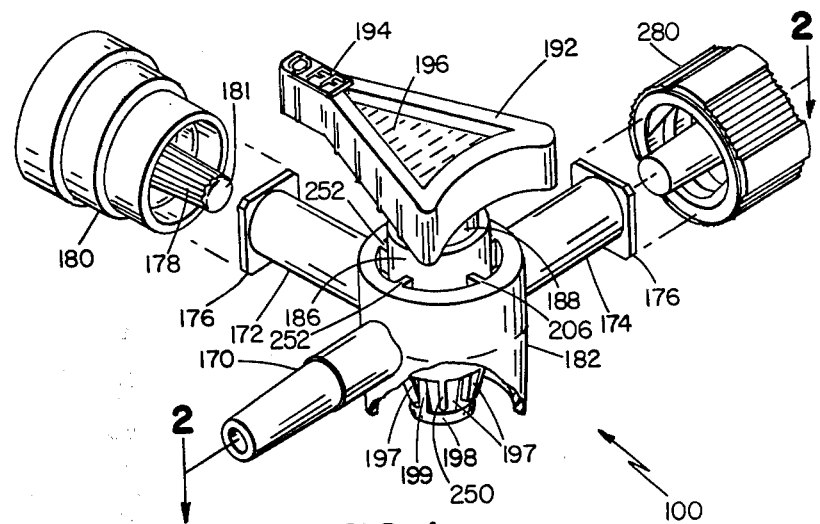
FIG. 1 is an isometric view of the presently preferred embodiment of the invention.
Figure 2:
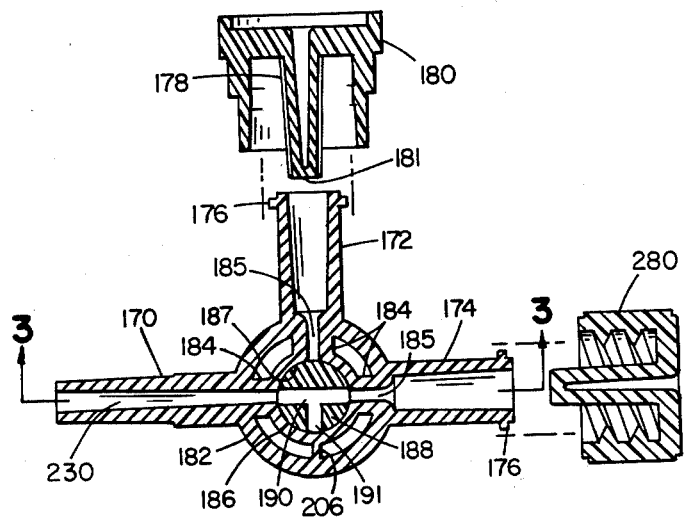
FIG. 2 is a sectional view taken through 2—2 of FIG. 1.
Figure 3:
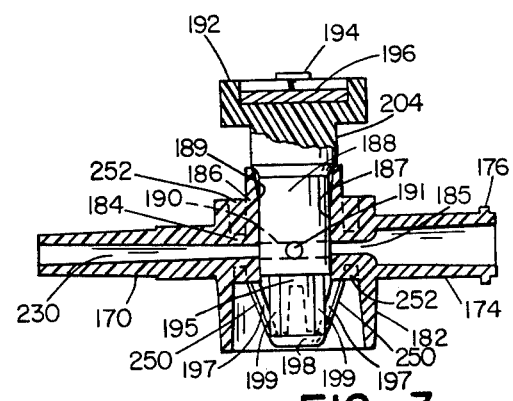
FIG. 3 is a sectional view taken through 3—3 of FIGS. 1 and 2.

Stopcock 100 has a male inlet tube 170 which is adapted for connection to either tubing or a female Luer lock fitting and may be adapted for connection to a reservoir. Spaced 90° and 180° from inlet tube 170 are outlet fittings 172, 174 each with female Luer lock fitting 176 and each capable of mating with vented cap 180, Luer lock cap 280, or with flexible tubing (not shown). A plurality of stopcocks can be connected together by inserting one stopcocks's inlet tube 170, which is tapered, into either of fittings 172, 174 of another stopcock. Vented cap 180 has grooves 178 in central plug 181 to allow gas to escape from the outlet fitting. Inlet tube 179 and fittings 172, 174 are integral extensions of cylindrical valve body 182. Three smaller tubes 184 (FIGS. 2 and 3) connect inlet tube 170 and fittings 172, 174, respectively, with ports on bore 187 of cylindrical inner sleeve 186. Tapered inlet passage 230 extends from inlet tube 170 through its associated tube 184 to bore 187. Passages 185 connect the tapered interiors of fittings 172, 174 with bore 187. The transitions between passages 185 and the fitting interiors are rounded to smooth fluid flow through the valve. Strut portions 252 axially straddle tubes 184 to provide strength. Continuous strut 206 forms a fourth support spoke between valve body 182 and inner sleeve 186. Strut 206 is positioned directly opposite the plastic-injection region or gate (not shown) which is adjacent to the outside surface of valve body 182 and through which molten plastic is injected into the mold to form the stopcock. Strut 206 is by its location the principal conduit during molding through which molten plastic travels to reach inner sleeve 186. Valve body 182 and inner sleeve 186 and all parts integral with them are molded from transparent polycarbonate plastic. Use of transparent plastic allows detention of fluid-entrained bubbles that may be held in stopcock passages. Inner sleeve 186 surrounds cylindrical core 188 made from Delrin 500 (DuPont trademark) acetal. The core has passages 190, 191 forming a "T" cut through it for establishing fluid connections between inlet tube 170 and fittings 172, 174. Handle 192 with pointer 194 (labelled "OFF") and colored polystyrene triangular insert 196 is integral with core 188. Pointer 194 extends in a direction 180° from passage 191. Core 188 is retained in sleeve 186 by four inwardly tapered fingers 197 extending from and integral with the bottom of the sleeve and acting against annular lip 198 on the end of lower, radially-reduced cylindrical extension 195 of the core. For increased bending stiffness, each finger 197 has longitudinal ridge 250 angularly-centered on its outer surface. Assembly of the stopcock is achieved by simply pushing core 188 down into inner sleeve 186 until lip 198 snaps past fingers 197. As can be seen in FIGS. 1 and 2, lip 198 has an upper surface that is substantially normal to the longitudinal axis of core 188, and fingers 197 are angled radially inward toward the core. The inclination of this upper surface and the angle of fingers 197 permanently lock the core into the valve body, as pulling axially on the core does not cause the fingers to spread. To ease installation of core 188, the interior diameter of sleeve 186 is slightly enlarged at mouth 189. Further downward motion of core 188 is resisted by the interior surface of mouth 189, which acts as a seat for radially enlarged neck 204 of the core. Two detent ridges 199 spaced 180° apart extend radially outward from extension 195 into the grooves formed between fingers 197. Dow Corning 360 silicone fluid is used as a lubricant between core 188 and sleeve 186.

Valve body 182 has a 0.482 inch outside diameter and 0.061 inch wall thickness. Sleeve 186 has a 0.30 inch outside diameter and 0.050 inch wall thickness. Bore 187 is between 0.199 and 0.200 inch in diameter. Core 188 is between 0.202 and 0.204 in outside diameter in the axial region in contact with bore 187, for an interference fit. Fourth spoke 206 is 0.027 inch thick and is 0.23 inch long axially. Strut portions 252 are also 0.027 inch thick, and smaller tubes 184 have 0.120 inch outside diameters and 0.032 inch wall thicknesses. Inlet fitting 170 has an outside diameter of 0.180 inch at the cylindrical portion closest the valve body. Fittings 172 and 174 have 0.220 inch outside diameters. Core passages 190, 191 are 0.061 inch in diameter, just slightly larger than the 0.056 inch diameter of passages 185, 230 at bore 187.

OPERATION

To operate the stopcock, the pointer 194 (FIG. 1) is rotated to whichever of the three inlet and outlet ports is to be shut off, thereby providing a fluid path along passages 190, 191 between the two remaining ports. In the figures pointer 194 is aimed at fitting 172, and passage 190 completes the fluid connection between inlet tube 170 and fitting 174. As core 188 is turned 90° between ports, detent ridges 199 outwardly deflect opposed pairs of fingers 197, and then snap into the grooves formed between the fingers upon reaching the new position, thereby providing tactile position feedback for the operator at each 90° space position of handle 192. To shut off both outlet fittings 172, 174 from inlet tube 170, pointer 194 is rotated to inlet fitting 170. To connect both outlet fittings to the inlet tube, the pointer is rotated to a position 180° from fitting 172.

OTHER EMBODIMENTS

Other embodiments will occur to those skilled in the art. For example, the direction of fluid flow between fittings could be varied, a different number of fittings could surround cylinder 182, additional passages could be provided in core 188 above or below present passages 190, 191 to provide more intricate connection combinations between external fittings, and handle 192 could be oriented differently with respect to core 188.

INCORPORATION BY REFERENCE

I incorporate by reference the copending U.S. patent application of Donn D. Lobdell and Stephen J. Herman entitled "Gas Exchange Apparatus", Ser. No. 917,350, filed June 20, 1978, to illustrate one application of the invention as part of a blood oxygenator.

OTHER INVENTION

Separating the stopcock into an inner sleeve in which the valve core is received and an outer body on which fluid fittings are secured was the invention of Donn D. Lobdell.

What is claimed is:

1. In a stopcock valve including a plastic valve body with internal passages leading from external fittings to ports on an internal bore and including a plastic valve core received in said bore and having at least one radially-directed internal passage for connecting said ports, the improvement wherein said bore and a portion of said core are cylindrical, the external diameter of said core is larger than the internal diameter of said bore to achieve an interference fit, the cylindrical surfaces of said bore and core are sufficiently close to a perfect cylinder in shape to maintain an interference fit all around said cylindrical surfaces so as to prevent leakage from said ports, a plurality of fingers extend from said body, said fingers are angled radially inward toward the longitudinal axis of said bore and are capable of resilient radial motion with respect to said axis, said valve core includes a lip, said lip including
a tapered surface for deflecting said plurality of fingers radially outward as said core in installed by translation in a first longitudinal direction and
a retention surface substantially normal to said longitudinal axis for acting against the tips of said fingers to permanently lock said core into said body longitudinally once said fingers snap radially inward past said lip, said substantially normal inclination of said retention surface and said radially-inward angle of said fingers acting to prevent radial separation of said fingers under an axial force applied to said core in a second axial direction, opposite said first direction, thereby preventing said core from being removed from said body along said section direction.

2. The fluid valve of claim 1 further comprising detent means for providing tactile feedback to the user of said valve that a predetermined angular orientation of said valve core has been reached.

3. The fluid valve of claim 2 wherein said detent means comprise radially extending ridges on said core and grooves on said body cooperating with said ridges to define detent positions.

4. The fluid valve of claim 3 wherein there are a plurality of said fingers, peripheral spacing between adjacent said fingers forms said grooves, and said ridges radially deflect said fingers between detent positions.

5. The fluid valve of claim 1 wherein there are three of said ports on said bore, said three ports are positioned 90degrees apart, and said internal passage in said valve core connects three openings spaced 90 degrees apart, whereby in one angular orientation of said core said three openings are each aligned with one of said three ports, thereby establishing fluid communication between all said ports.

6. The fluid valve of claim 5 wherein said core further comprises a handle having a pointer, said pointer extending in a direction 180 degrees from the central opening of said three core openings, whereby said pointer on said valve body indicates the port on said bore not in fluid communication with the other said ports on said bore.

7. In a fluid valve including a valve body with internal passages leading from external fittings to ports on a bore and a valve core received in said bore and having an internal passage for connecting said ports, the improvement comprising:
   a plurality of fingers extending from said body and capable of resilient radial motion with respect to the longitudinal axis of said bore,
   lip means on said valve core for deflecting said fingers radially outward during longitudinal installation of said core in said body and for providing a retention surface against which said fingers act upon full installation to lock said core into said body longitudinally, and
   detent means for providing tactile feedback to the user of said valve that a predetermined angular orientation of said valve core has been reached, said detent means comprising radially extending ridges to define detent positions, the peripheral spacing between adjacent said fingers forming said grooves, and said ridges radially deflecting said fingers between detent positions.

8. The fluid valve of claim 1 or 7 wherein there are four said fingers.

* * * * *

UNITED STATES PATENT AND TRADEMARK OFFICE
CERTIFICATE OF CORRECTION

PATENT NO. : 4,207,923
DATED : June 17, 1980
INVENTOR(S) : Joel F. Giurtino

It is certified that error appears in the above-identified patent and that said Letters Patent are hereby corrected as shown below:

Column 2, line 24, "stopcocks's" is changed to
--stopcock's--.

Column 2, line 28, "Inlet tube 179" is changed to
--Inlet tube 170--.

Column 2, line 50, "allows detention" is changed to
--allows detection--.

Column 3, line 6, "to spread." is changed to
--to spread apart.--.

Column 3, line 35, "the pointer 194" is changed to
--pointer 194--.

Column 3, line 46, "space position" is changed to
--spaced position--.

Column 4, claim 1, line 28, "core in installed" is changed to
--core is installed--.

Column 4, claim 1, line 41, "section direction" is changed to
--second direction--.

Signed and Sealed this

Ninth Day of September 1980

[SEAL]

Attest:

SIDNEY A. DIAMOND

Attesting Officer

Commissioner of Patents and Trademark